United States Patent [19]
Cragg et al.

[11] Patent Number: 6,071,301
[45] Date of Patent: Jun. 6, 2000

[54] DEVICE AND METHOD FOR FACILITATING HEMOSTASIS OF A BIOPSY TRACT

[75] Inventors: Andrew H. Cragg, Edina, Minn.; Rodney Brenneman, San Juan Capistrano; Mark Ashby, Laguna Niguel, both of Calif.

[73] Assignee: SUB Q., Inc., Edina, Minn.

[21] Appl. No.: 09/071,670

[22] Filed: May 1, 1998

[51] Int. Cl.[7] .............................. A61B 17/08; A61M 5/32
[52] U.S. Cl. ............................................ 606/213; 604/265
[58] Field of Search ...................................... 606/212–214; 604/51–54, 48, 2, 1, 15, 264, 265, 270, 59, 60, 38

[56] References Cited

U.S. PATENT DOCUMENTS

| | | |
|---|---|---|
| 581,235 | 4/1897 | Kenyon . |
| 1,578,517 | 3/1926 | Hein . |
| 2,086,580 | 7/1937 | Shirley . |
| 2,465,357 | 3/1949 | Correll . |

(List continued on next page.)

FOREIGN PATENT DOCUMENTS

| | | |
|---|---|---|
| 0 032 826 | 7/1981 | European Pat. Off. . |
| 0 476 178 | 3/1992 | European Pat. Off. . |
| 0 482 350 | 4/1992 | European Pat. Off. . |
| 2 641 692 | 7/1990 | France . |
| 782 814 | 11/1980 | Russian Federation . |
| 1 088 709 | 4/1984 | Russian Federation . |
| 1 509 023 | 4/1978 | United Kingdom . |
| 1 569 660 | 6/1980 | United Kingdom . |
| WO 98/06346 | 2/1988 | WIPO . |
| WO 96/08208 | 3/1996 | WIPO . |

OTHER PUBLICATIONS

Vinant Chuang, M.D., et al., "Sheath Needle for Liver Biopsy in High–Risk patients," Technical Developments and Instrumentation, Radiology, vol. 166, (1988): pp. 261–262.

Tony P. Smith, et al., "Percutaneous Transhepatic Liver Biopsy with Tract Embolization," Radiology, vol. 198 (1996): pp. 769–774.

S.A. Riley, et al., :"Percutaneous Liver Biopsy With Plugging of Needle Tract: A Safe Method For Use In Patients With Impaired Coagulation," The Lancet (Aug. 1964).

Sigmund Silber, M.D., "Rapid Hemostasis of Arterial Puncture Sites with Collagen in Patients Undergoing Diagnostic and Interventional Cardiac Catheterization," Clinical Cardiology, vol. 20, (Dec. 1997): pp. 981–992.

Marc Zins, M.D., et al., "US–guided Percutaneous Liver Biopsy with Plugging of the Needle Track: A Prospective Study in 72 High–Risk Patients," Radiology, vol. 184 (1992): pp. 841–843.

David J. Allison, M.D., et al. "Percutaneous Liver Biopsy and Tract embolization with Steel Coils," Radiology, vol. 169 (1998) pp. 261–263.

(List continued on next page.)

*Primary Examiner*—Michael Buiz
*Assistant Examiner*—Vikki Trinh
*Attorney, Agent, or Firm*—Burns Doane Swecker & Mathis L.L.P.

[57] ABSTRACT

A system including an adaptor and a syringe is used for facilitating hemostasis of a biopsy tract or other puncture wound by injection of an absorbable sponge in a hydrated state into the wound. The adaptor includes a tapered lumen for hydrating and compressing the relatively large absorbable sponge for delivery through a relatively small cannula, such as a biopsy needle. The hydrated absorbable sponge is injected through the biopsy needle into the biopsy tract by fluid. The implanted absorbable sponge facilitates hemostasis at the biopsy site or other puncture wound and minimizes the chance of internal bleeding. The absorbable sponge material is absorbed by the body over time.

30 Claims, 4 Drawing Sheets

U.S. PATENT DOCUMENTS

| | | |
|---|---|---|
| 2,492,458 | 12/1949 | Bering, Jr. . |
| 2,507,244 | 5/1950 | Correll . |
| 2,558,395 | 6/1951 | Studer . |
| 2,597,011 | 5/1952 | MacMasters et al. . |
| 2,680,442 | 6/1954 | Linzmayer . |
| 2,761,446 | 9/1956 | Reed . |
| 2,814,294 | 11/1957 | Figge . |
| 2,824,092 | 2/1959 | Thompson . |
| 2,899,362 | 8/1959 | Sieger, Jr. et al. . |
| 3,157,524 | 11/1964 | Artandi . |
| 4,000,741 | 1/1977 | Binard et al. . |
| 4,323,072 | 4/1982 | Rosenbluth et al. . |
| 4,340,066 | 7/1982 | Shah . |
| 4,390,018 | 6/1983 | Zulowski . |
| 4,515,637 | 5/1985 | Cioca . |
| 4,587,969 | 5/1986 | Gillis . |
| 4,588,395 | 5/1986 | Lemelson . |
| 4,619,261 | 10/1986 | Guerriero . |
| 4,619,913 | 10/1986 | Luck et al. . |
| 4,645,488 | 2/1987 | Matukas . |
| 4,744,364 | 5/1988 | Kensey . |
| 4,790,819 | 12/1988 | Li et al. . |
| 4,829,994 | 5/1989 | Kurth . |
| 4,850,960 | 7/1989 | Grayzel . |
| 4,852,568 | 8/1989 | Kensey . |
| 4,890,612 | 1/1990 | Kensey . |
| 4,900,303 | 2/1990 | Lemslson . |
| 4,929,246 | 5/1990 | Sinofsky . |
| 4,936,835 | 6/1990 | Haaga . |
| 4,950,234 | 8/1990 | Fujioka et al. . |
| 5,007,895 | 4/1991 | Burnett . |
| 5,021,059 | 6/1991 | Kensey et al. . |
| 5,053,046 | 10/1991 | Janese . |
| 5,061,274 | 10/1991 | Kensey . |
| 5,080,655 | 1/1992 | Haaga . |
| 5,108,421 | 4/1992 | Fowler . |
| 5,163,904 | 11/1992 | Lampropoulos et al. . |
| 5,167,624 | 12/1992 | Butler et al. . |
| 5,192,300 | 3/1993 | Fowler . |
| 5,192,301 | 3/1993 | Kamiya et al. . |
| 5,195,988 | 3/1993 | Haaga . |
| 5,220,926 | 6/1993 | Jones . |
| 5,221,259 | 6/1993 | Weldon et al. . |
| 5,275,616 | 1/1994 | Fowler . |
| 5,310,407 | 5/1994 | Casale . |
| 5,325,857 | 7/1994 | Nabai et al. . |
| 5,334,216 | 8/1994 | Vidal et al. . |
| 5,366,480 | 11/1994 | Corriveau et al. . |
| 5,383,896 | 1/1995 | Gershony et al. . |
| 5,383,899 | 1/1995 | Hammmerslag . |
| 5,388,588 | 2/1995 | Nabai et al. . |
| 5,391,183 | 2/1995 | Janzen et al. . |
| 5,419,765 | 5/1995 | Weldon et al. . |
| 5,431,639 | 7/1995 | Shaw . |
| 5,437,631 | 8/1995 | Janzen . |
| 5,467,780 | 11/1995 | Nabai et al. . |
| 5,478,352 | 12/1995 | Fowler . |
| 5,479,936 | 1/1996 | Nabai et al. . |
| 5,486,195 | 1/1996 | Myers et al. . |
| 5,522,850 | 6/1996 | Yomtov et al. . |
| 5,526,822 | 6/1996 | Burbank et al. . |
| 5,529,577 | 6/1996 | Hammerslag . |
| 5,540,715 | 7/1996 | Katsaros et al. . |
| 5,545,178 | 8/1996 | Kensey et al. . |
| 5,558,853 | 9/1996 | Quay . |
| 5,591,204 | 1/1997 | Janzen et al. . |
| 5,591,205 | 1/1997 | Fowler . |
| 5,601,602 | 2/1997 | Fowler . |
| 5,645,566 | 7/1997 | Brennenman et al. . |
| 5,649,547 | 7/1997 | Ritchart et al. . |
| 5,653,730 | 8/1997 | Hammerslag . |
| 5,665,107 | 9/1997 | Hammerslag . |
| 5,681,279 | 10/1997 | Rober et al. . |
| 5,716,375 | 2/1998 | Fowler . |
| 5,725,498 | 3/1998 | Janzen et al. . |
| 5,741,223 | 4/1998 | Janzen et al. . |
| 5,769,086 | 6/1998 | Ritchart et al. . |
| 5,775,333 | 7/1998 | Burbank et al. . |
| 5,810,806 | 9/1998 | Ritchart et al. . |
| 5,830,130 | 11/1998 | Janzen et al. . |
| 5,902,310 | 5/1999 | Foerster et al. . |
| 6,027,471 | 2/2000 | Fallon et al. ........................ 606/213 X |

OTHER PUBLICATIONS

Ferdinand Kiemeneij, M.D., et al., "Improved Anticoagulation Management After Palmaz Schatz Coronary Stent Implantation by Sealing the Arterial Puncture Site With a Vascular Hemostasis Device," Catheterization and Cardiovascular Diagnosis, vol. 30, (1993): pp. 317–322.

J.P.M. Foran, et al., "Early Mobilization After Percutaneous Cardiac Catheterisation Using Collagen Plug(VasoSeal) Haemostasis," Br. Heart, vol. 69 (1993) pp. 424–429.

R. Schrader, et al., "Percutaneous Collagen Application," Catheterization and Cardiovascular Diagnosis (1992): pp. 298–302.

J.S.R. Gibbs, et al., "Femoral Arterial Hemostasis Using a Collagen Plug After Coronary Artery Stent Implanation," Journal of Interventional Cadiology, vol. 5, No. 2 (1992): 85–88.

William G. Kussmaul III, M.D., et al., "Rapid Arterial Hemostasis and Decreased Access Site Complications After Cardiac Catheterization and Angioplasty: Results of a Randomized Trial of a Novel Hemostatic Device," Journal of the American College of Cardiology, vol. 25, No. 7 (1995): pp. 1685–1692.

Timothy A. Sanborn, M.D., et al., "Multicenter Randomized Trial Comparing a Percutaneous Collagen Hemostasis Device With Conventional Manual Compression After Diagnostic Angiography and Angioplasty," Journal of the American College of Cardiology, vol. 25, No. 7 (1993): pp. 1273–1279.

Pharmacia & Upjohn Manufacturer Brochure *"Gelfoam Sterile Sponge, Sterile Powder, and Sterile Film,"* (May 1997): pp. 1–34.

Pharmacia & Upjohn Manufacturer Brochure *"Gelfoam Sterile Powder,"* (Mar. 1996).

Pharmacia & Upjohn Manufacturer Specification *"Gelfoam Sterile Sponge, Sterile Powder, and Sterile Film,"* (Nov. 1996): pp. 1–23.

Pharmacia & Upjohn Manufacturer Brochure, "Gelfoam Sterile Powder," Feb. 1996.

Pharmacia & Upjohn Manufacturer Brochure for Gelfoam, Sep. 1996.

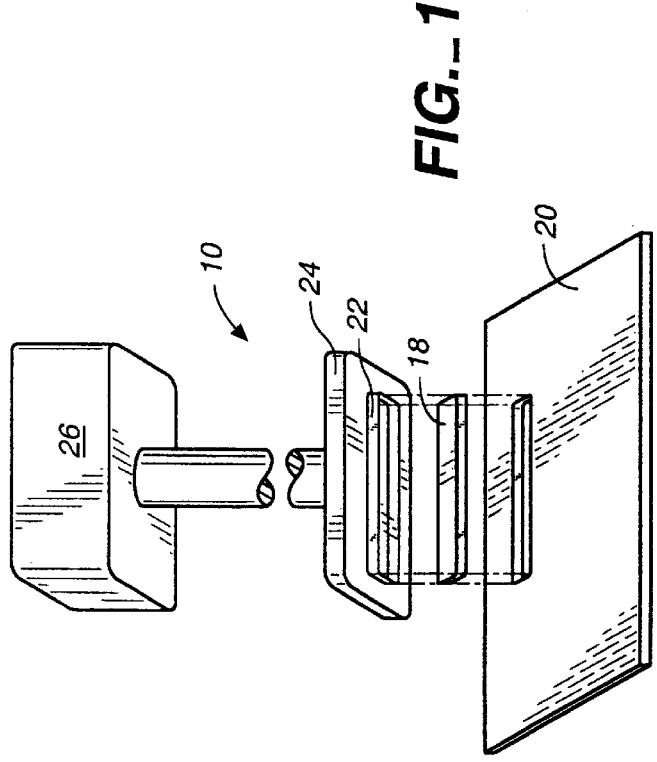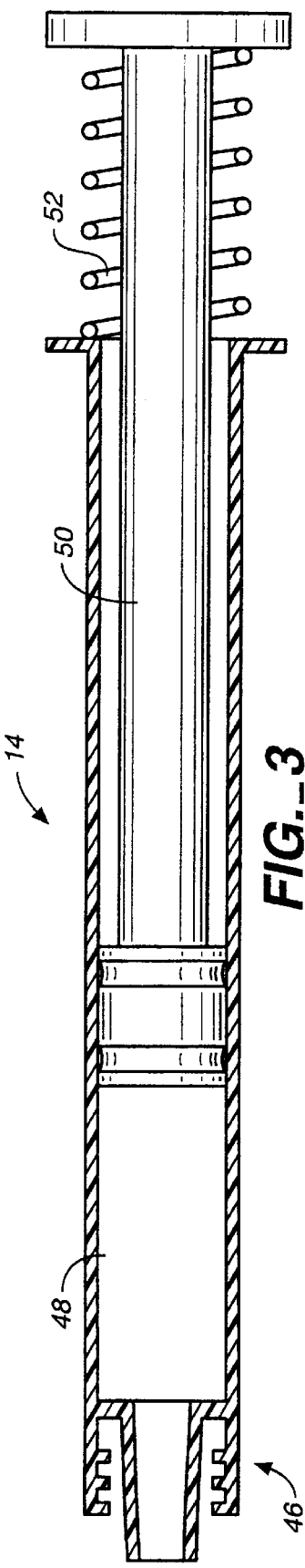

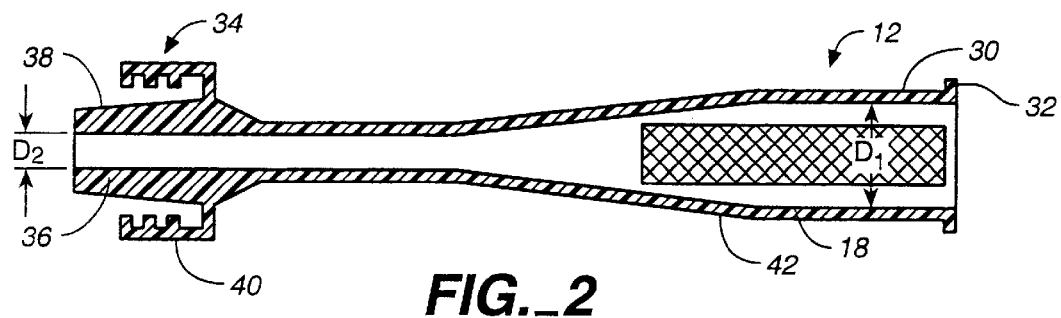
FIG._2
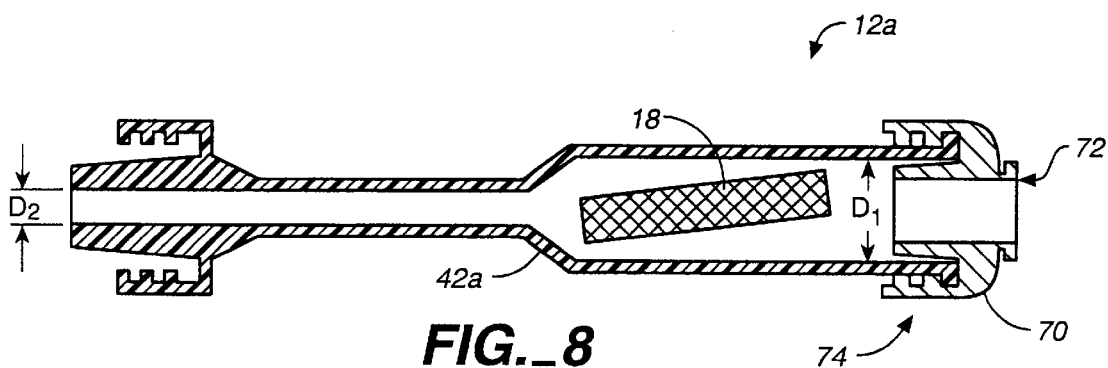
FIG._8
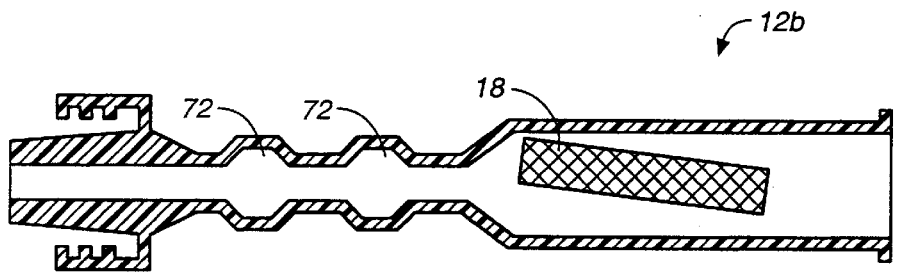
FIG._9
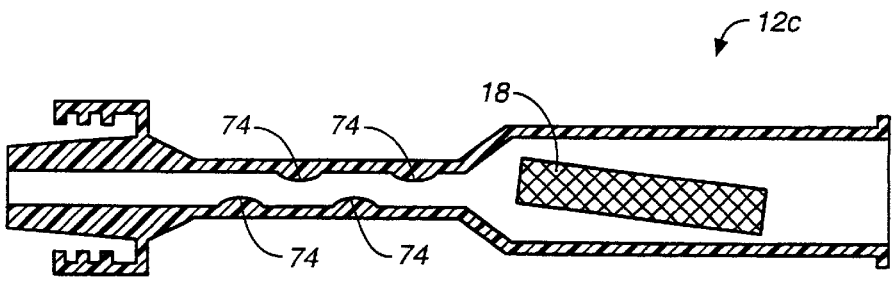
FIG._10

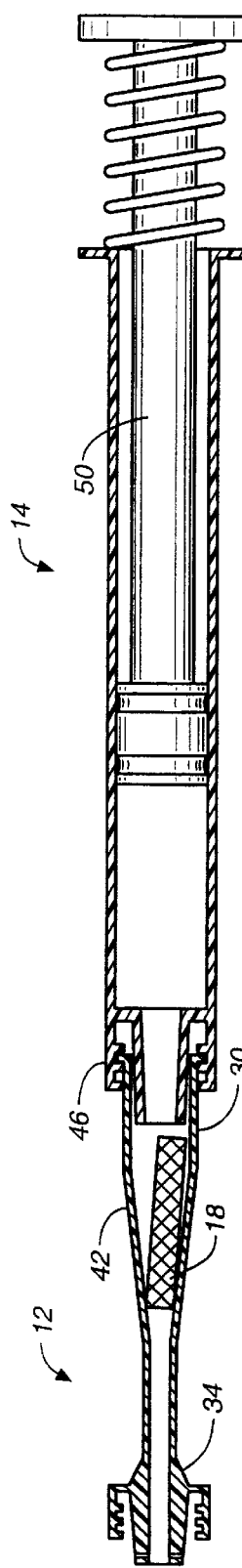
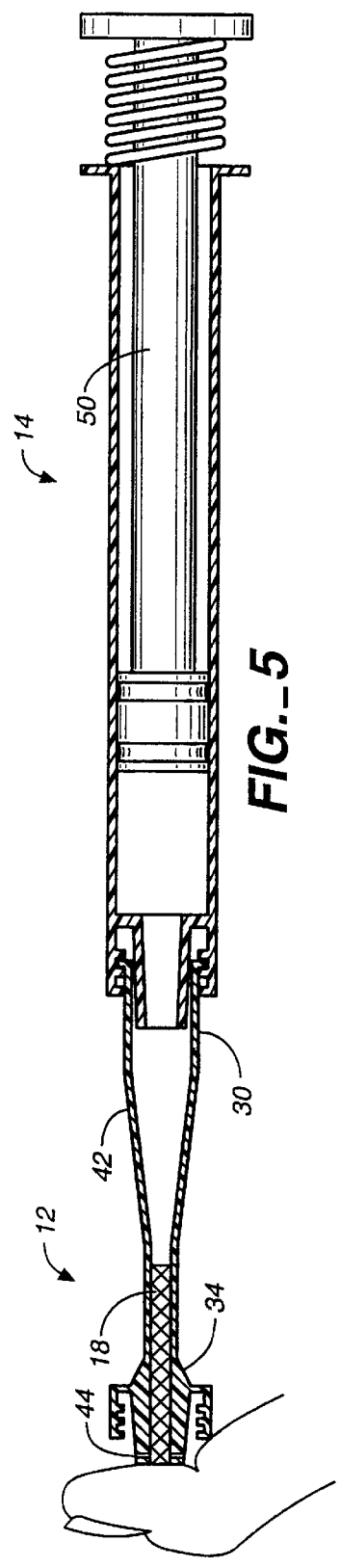
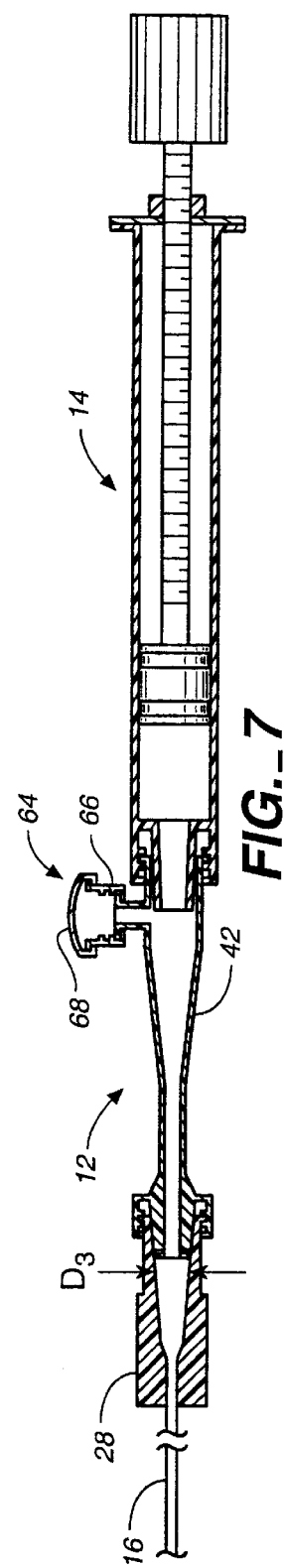

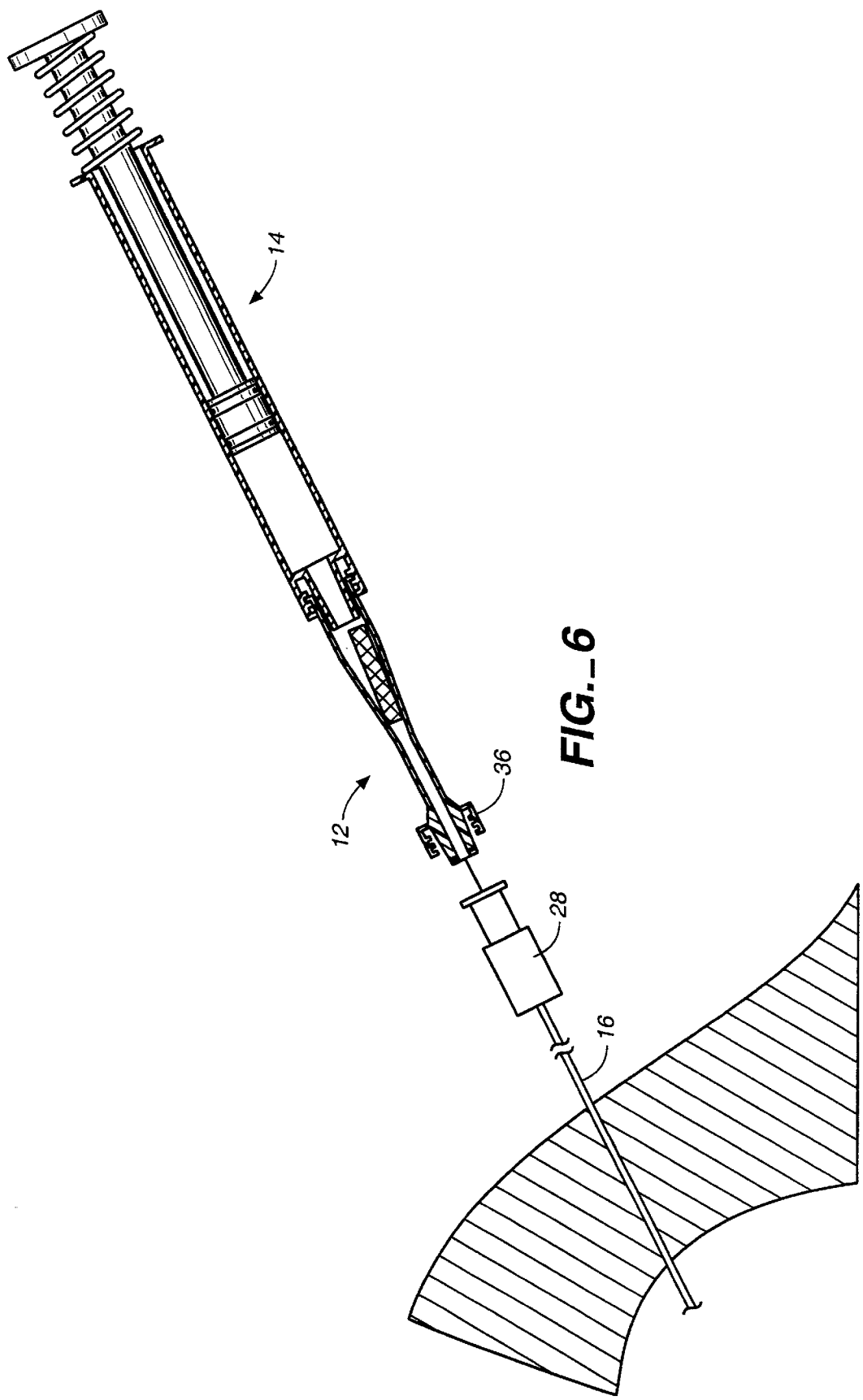
FIG._6

DEVICE AND METHOD FOR FACILITATING HEMOSTASIS OF A BIOPSY TRACT

BACKGROUND OF THE INVENTION

1. Field of the Invention

The invention relates to a wound closure device, and more particularly, the invention relates to a device and method for facilitating hemostasis of a biopsy tract or other puncture wound by injection of an absorbable sponge.

2. Brief Description of the Related Art

Percutaneous needle biopsy of solid organs is one of the most common interventional medical procedures. Millions of percutaneous needle biopsies are performed annually in the United States and throughout the world. Percutaneous biopsy is a safe procedure which has supplanted surgical biopsy for many indications, such as skin biopsy and liver biopsy.

Possible complications of needle biopsy include bleeding at the biopsy site. The amount of bleeding is related to a number of factors including needle size, tissue sample size, patient's coagulation status, and the location of the biopsy site. Vascular organs such as the liver, a common biopsy target, may bleed significantly after needle biopsy. To minimize bleeding from a biopsy site, small-gauge needles are typically used. Small gauge needles, however, produce less satisfactory biopsy specimens but frequently are favored over larger bored needles because of their perceived safety. In order to minimize the chance of internal bleeding after biopsy, external pressure is applied and patients are often asked to lie in uncomfortable positions, such as the lateral decubitus position, for a number of hours, particularly after liver biopsy.

Sterile sponges, such as Gelfoam, are prepared in dry sterile sheets which are used as packing material during surgery for control of bleeding. The sponge sheets are left in the surgical site after surgery to stop bleeding and are absorbed by the body in 1 to 6 weeks. A number of techniques have used these absorbable sterile sponge materials to plug a biopsy tract to minimize or prevent bleeding. The absorbable sponge provides a mechanical blockage of the tract, encourages clotting, and minimizes bleeding though the biopsy tract. Despite the advantages of using absorbable sponge to plug a biopsy tract this technique has not achieved widespread use because of difficulty in preparing and delivering the sponge material into the biopsy tract.

One example of a biopsy wound closure device using an implantable sponge is described in U.S. Pat. No. 5,388,588. According to this patent, a circular sponge of an absorbable foam material is precut and inserted into a biopsy site by an applicator rod having the sponge positioned on the end. Once the sponge is implanted, the sponge absorbs blood and swells to fill the tract preventing further bleeding at the biopsy site. However, the sponge is difficult to deliver and expands slowly once delivered. In addition, this delivery method can only deliver a sponge of a limited size which provides less local compression than desired and may incompletely fill the target site.

Accordingly, it would be desirable to provide a device and method which will permit the delivery of an absorbable sponge to a biopsy tract in a simple and reliable manner.

SUMMARY OF THE INVENTION

The present invention relates to a device and method for facilitating hemostasis of a biopsy tract or other puncture wound by injecting an absorbable sponge. The system according to the present invention allows the sponge to be delivered in a hydrated state through the biopsy needle or other cannula directly into the puncture wound.

In accordance with one aspect of the present invention, a system for facilitating hemostasis of a puncture wound by injecting an absorbable sponge includes a cannula for delivering the absorbable sponge in the hydrated state to the puncture wound, an adapter connectable to the cannula, and a syringe for injecting fluid into the adaptor to hydrate and deliver the absorbable sponge. The adaptor includes a tapered lumen with a large diameter end and a small diameter end, wherein the small diameter end is connectable to the cannula.

In accordance with an additional aspect of the present invention, an adaptor for delivering a hydrated absorbable sponge to a cannula for facilitating hemostasis of a puncture wound includes an elongated member having a first end, a second end and a lumen extending from the first end to the second end. A luer connector is provided at the second end of the elongated member for connection to a cannula. A tapered section of the lumen tapers from a first diameter at the first end to a second diameter at the second end which is smaller than the first diameter such that a dry sponge pledget having a width larger than the second diameter is compressable, when hydrated, into the second diameter.

In accordance with a further aspect of the invention, a method of facilitating hemostasis of a puncture wound by injecting an absorbable sponge through a cannula into the puncture wound includes the steps of inserting a pledget of an absorbable sponge into an adaptor having a tapered lumen with a large diameter end and a small diameter end; hydrating the pledget by injection of fluid into the adaptor; connecting the adaptor to a cannula; and delivering the hydrated absorbable sponge through the cannula to facilitate hemostasis of the puncture wound.

In accordance with an additional aspect of the present invention, a method of facilitating hemostasis of a biopsy tract includes steps of removing a tissue biopsy through a cannula, and injecting a hydrated absorbable sponge pledget through the cannula without fully removing the cannula from the biopsy tract to facilitate hemostasis of the biopsy tract.

According to another additional aspect of the present invention, a kit for facilitating hemostasis of a puncture wound includes a pledget forming device, an adaptor connectable to a cannula for hydrating and delivering an absorbable sponge pledget to the cannula, the adapter having a tapered lumen with a large diameter end and a small diameter end, wherein the small diameter end is connectable to the cannula, and a syringe connectable to the adaptor for delivering fluid to the adaptor.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a perspective view of a punch for forming pledgets;

FIG. 2 is a side cross sectional view of an adaptor for delivery of a pledget to a needle;

FIG. 3 is a side cross sectional view of a syringe for connection to the adaptor;

FIG. 4 is a side cross sectional view of an adaptor and syringe combination with a pledget positioned within the adaptor;

FIG. 5 is a side cross sectional view of an adaptor and syringe combination in accordance with an alternative embodiment in which the pledget has been hydrated and moved into a small diameter end of the adaptor;

FIG. 6 is a side cross sectional view of the loaded adaptor and syringe combination in preparation for connection to a biopsy needle;

FIG. 7 is a side cross sectional view of an alternative embodiment of an adaptor connected to a biopsy needle and syringe;

FIG. 8 is a side cross sectional view of an alternative embodiment of an adaptor;

FIG. 9 is a side cross sectional view of an alternative embodiment of an adaptor with enlargements in the lumen for kneading the pledget; and FIG. 10 is a side cross sectional view of an alternative embodiment of an adaptor with irregularities in the lumen for kneading the pledget.

DETAILED DESCRIPTION OF THE PREFERRED EMBODIMENTS

The system of the present invention delivers an absorbable sponge material in a hydrated state to facilitate hemostasis of a biopsy tract or other puncture wound in a simple and safe manner. The apparatus for delivering a hydrated absorbable sponge will be described below in connection with treatment of a biopsy tract after a percutaneous needle biopsy. However, the invention may be used for facilitating hemostasis of other types of puncture wounds to prevent bleeding of these wounds.

The system for facilitating hemostasis of the biopsy tract includes a punch 10 for cutting a pledget 18 of absorbable sponge material from a sheet of this material, an adaptor 12 for delivering the pledget to a biopsy needle 16, and a syringe 14 for hydrating and injecting the pledget. The adaptor 12 allows a relatively large pledget of absorbable sponge material to be compressed and inserted into the biopsy tract in a hydrated state. The absorbable sponge material for use in facilitating hemostasis may be any absorbable sponge which is capable of deforming upon hydration to be delivered by fluid pressure through a biopsy needle or other cannula.

Prior to discussing the present invention in further detail, the following terms are defined:

"Pledget" means a piece of absorbable sponge of a generally elongated shape having a size which allows injection in a hydrated state through a biopsy needle or other cannula.

"Absorbable sponge" means a biocompatible material which is capable of being hydrated, is resiliently compressible in a hydrated state, and when implanted within a human or other mammalian body is absorbed by the body. Preferably, the absorbable sponge is non-immunogenic.

"Hydrate" means to partially or fully saturate with a fluid, such as, saline, water, contrast agent, thrombin, therapeutic agent, or the like.

"Kneading" of the absorbable sponge material means both dry and wet manipulation of sponge material which compresses, enlarges, or changes the shape of the sponge material causing the sponge material to have improved expansion response.

FIG. 1 illustrates one example of a punch 10, also called a dye cutter, for cutting an absorbable sponge sheet 20 into pledgets 18 of an appropriate size for delivery to a biopsy tract. The punch 10 includes a rectangular blade 22 fixed to a plate 24 having a handle 26. The punch 10 is pressed down onto a flat sheet 20 of commercially available absorbable sponge to cut the pledget 18 of an appropriate size. In addition to the punch 10 illustrated in FIG. 1 other cutting devices, such as, a scissor type hand punch, an automatic punching machine, or a templet and knife may be used for preparation of the pledget 18.

FIG. 2 shows the adaptor 12 according to the present invention in which the pledget 18 is placed for hydration and for delivery through the biopsy needle 16. The adaptor 12 allows pieces of absorbable sponge material with relatively large cross sections to be easily delivered through a biopsy needle 16 with a much smaller cross section. The adaptor 12 also functions to remove air from the pledget 18.

The adaptor 12 which delivers the hydrated pledget 18 to the needle 16 includes a first end 30 having an annular lip 32 or female luer fitting for connection to the syringe 14. A second end 34 of the adaptor 12 has a male luer fitting 36 for connection to a biopsy needle 16 or other cannula. The luer fitting 36 includes a tapered external surface 38 and a retaining ring 40 with internal threads for receiving an annular lip of the biopsy needle. The adaptor 12 has an internal lumen with a first diameter $D_1$ at the first end 30 and a second diameter $D_2$ at the second end 34. Between the first and second ends of the adaptor 12 a tapered section 42 of the adaptor provides a funnel for compressing the hydrated pledget 18 prior to injection through the biopsy needle 16 and needle hub 28.

The adaptor 12 may be formed in any known manner such as by molding from a plastic material. Preferably, the adaptor 12 is transparent so that the pledget 18 can be viewed through the adaptor and the user can visually monitor when the pledget is loaded within the adaptor and when the pledget has been delivered into the needle. The adaptor lumen may be provided with a friction reducing coating for improved delivery. The delivery fluid also reduces friction for improved delivery by wetting the exterior surface of the pledget.

The syringe 14 includes a male luer fitting 46, a fluid chamber 48, and a plunger 50. The first end 30 of the adaptor 12 is connectable to the luer fitting 46 of the conventional syringe 14. The syringe 14 may be provided with a spring 52 for automatic filling of the syringe 14 with a predetermined volume of fluid. Alternatively, the syringe may include a threaded syringe plunger, as shown in FIG. 7, for accurate injection of small quantities of fluid. The syringe volume will vary depending on the amount of fluid needed for hydration and delivery of the pledget 18 through the biopsy needle 16.

A biopsy needle 16 for use with the present invention is preferably a coaxial biopsy needle, such as a bi-axial or a tri-axial biopsy needle. A co-axial biopsy needle includes an outer needle or cannula through which a tissue sample is removed with a tissue scoop or other biopsy instrument. Once the tissue sample has been removed, the outer cannula remains in the patient as illustrated in FIG. 6

A preferred method of facilitating hemostasis of a biopsy tract will be described with reference to FIG. 4 which shows the loading and hydration of the pledget 18 within the adaptor 12. A pledget 18 is cut as described above and placed within the adaptor 12 from the first end 30 of the adaptor. The syringe 14 is filled with a predetermined amount of fluid, such as saline, and is connected to the first end 30 of the adaptor 12 by the luer fitting 46. The plunger 50 of the syringe 14 is then depressed slowly causing fluid to pass into the adaptor 12, hydrating the pledget 18, and filling the adaptor with a column of fluid. Care should be taken to inject the fluid slowly to prevent the pledget from being ejected out of the second end 34 of the adaptor. Preferably, the user waits a few seconds once the fluid is injected into the adaptor 12 until the pledget 18 is adequately hydrated creating a lubricous surface on the pledget. The pledget 18 may expand within the adaptor to fill or nearly fill the lumen of the adaptor. The adaptor 12 with the pledget 18 hydrated within the proximal end is ready to inject the pledget into a biopsy tract to facilitate hemostasis within the biopsy tract. The adaptor 12 may be loaded prior to beginning the biopsy procedure.

After the biopsy procedure has been completed, the outer sheath of the biopsy needle 16 through which the biopsy has been taken is maintained in place within the biopsy tract, as shown in FIG. 6. The biopsy needle 16 provides preestablished targeting of the delivery site for delivery of the absorbable sponge pledget 18 and eliminates the uncertainty of re-access. The luer fitting 36 of the adaptor 12 is connected to the biopsy needle hub 28, as illustrated in FIG. 6. The biopsy needle 16 is withdrawn a short distance, such as about 1 to 20 mm, along the biopsy tract to provide space for the pledget 18 to be received in the biopsy tract. Additional fluid is then rapidly injected by the syringe to move the pledget 18 into the biopsy needle 16. When the adaptor lumen has been blocked by the hydrated pledget 18 which has swelled within the adaptor, injection of additional fluid will push the pledget through the tapered section 42 of the adaptor. If the adaptor lumen has not been entirely blocked by the pledget 18, the venturi effect will help draw the pledget through the tapered section 42 of the adaptor. After the pledget 18 is moved to the biopsy needle 16, the pledget 18 is then delivered from the needle 16 to the biopsy tract by rapid injection of additional fluid by the syringe 14. The hydrated pledget 18 quickly expands upon delivery to fill the available space in the biopsy tract to facilitate hemostasis and provide localized compression.

As illustrated in the cross sectional view of FIG. 7, one example of a needle hub 28 has an interior diameter $D_3$ which is larger than the diameter $D_2$ at the distal end 36 of the adaptor 12. The large internal diameter needle hub 28 allows the hydrated pledget 18 which has been compressed by the tapered section 42 of the adaptor to expand in the needle hub before being compressed again into the needle lumen. This compression and enlargement of the hydrated absorbable sponge material, does not adversely effect the pledget delivery and in fact improves the expansion response of some delivered sponge materials as will be discussed in further detail below.

A smooth tapered transition between the lumen of the needle hub 28 and the needle lumen helps to provide for easy injection of the pledget 18. However, needles having internal steps between the needle hub 28 and the needle 16 have been used and the pledget 18 is still injected successfully. According to an alternative embodiment of the invention, the needle hub 28 may be designed to have a inner diameter approximately the same as the inner diameter $D_2$ at the distal end 36 of the adaptor.

Preferably, specific measured doses of fluid are used to achieve each of the steps of the treatment procedure depending on the pledget size and the dimensions of the adaptor 12, the needle 16, and the needle hub 28. The pledget 18 should be completely delivered into the biopsy tract by the fluid and only a minimal amount of extraneous fluid should be delivered. For example, the pledget 18, once inside the needle, may be delivered with about 0.02 to 0.03 ml of fluid. Injection of larger amounts of fluid may distend the biopsy tract or displace the pledget within the organ.

According to one example, a pledget 18 having a size of approximately 20 mm by 2 mm cut from a sheet of commercially available Gelfoam having a thickness of approximately 1.5 mm can be hydrated and injected through a standard 18 gauge, approximately 15 cm long biopsy needle with approximately 0.9 ml of fluid. An adaptor according to this example has a first diameter $D_1$ of about 0.38 cm, a second diameter $D_2$ of about 0.14 cm, a total length of about 3.80 cm, and a taper angle of about 45°. About 0.3 ml of fluid is injected slowly to hydrate the pledget 18 and fill the adaptor with a column of fluid. Approximately 0.3 ml of fluid is then injected to load the pledget 18 from the adaptor 12 into the biopsy needle 16. Finally, about 0.3 ml of fluid is injected to deliver the pledget 18 into the biopsy tract. Loading of the pledget from the adaptor 12 into the needle 16 and delivery from the needle to the biopsy tract can be combined in one step by delivery of approximately 0.6 ml. Accurate and complete injection of the pledget with a minimum amount of extraneous fluid is achieved by this volumetric injection technique.

According to an alternative embodiment of the adaptor illustrated in FIG. 5, vent holes 44 extend through the side walls of the adapter 12 adjacent the second end 34 for venting fluid during loading of the pledget 18. As illustrated in FIG. 4, the user places a finger over the second end 34 of the adaptor 12 to prevent the pledget from exiting the adaptor. The plunger 50 of the syringe 14 is then depressed slowly causing fluid to pass into the adaptor 12 and hydrate the pledget. Preferably, the user waits a few seconds once the fluid is injected into the adaptor 12 until the pledget 18 is hydrated. Once the pledget 18 is hydrated, additional fluid is then injected quickly into the adaptor 12 to move the pledget 18 from the first end 30 of the adaptor towards the second end 34 of the adaptor. As the pledget 18 is compressed by the tapered section 42 of the adaptor 12 air and fluid are allowed to escape from the adaptor through the vent holes 44. Once the pledget 18 has been moved into the positioned illustrated in FIG. 5 adjacent the second end 34, fluid injection is halted. The adaptor 12 with the hydrated pledget 18 within the distal end is ready to insert the pledget through a biopsy needle to facilitate hemostasis within the biopsy tract.

As an alternative to placement of a finger at the distal end of the adaptor 12 during advancement of the pledget 18 through the tapered section 42, a removable cap may be used. Further, the vent holes 44 may be omitted and a screen or a cap having a screen may be used to allow fluid to pass through the screen while the screen prevents the pledget 18 from being ejected.

An alternative embodiment of the delivery system is illustrated in FIG. 7 in which an adaptor 12 is provided with a pressure indicator 64 to monitor pledget injection. Preferably, the pressure indicator 64 is removably attached at a luer fitting 66 provided on a side of the adaptor 12. The pressure indicator 64 includes a pressure dome 68 movable from the convex shaped extended position illustrated in FIG. 7 to a flat position depending on the pressure inside the adaptor 12. Internal pressure within the biopsy needle 16, the adaptor 12, and the syringe 14 will drop as the pledget 18 is extruded from the biopsy needle into the biopsy tract. This causes the pressure dome 68 to move from the convex position illustrated in FIG. 7 to a flat position, indicating that pledget delivery is complete.

FIG. 8 illustrates an alternative embodiment of an adaptor 12a in which the tapered section 42a is shorter and more abrupt. The particular size and shape of the adaptor 12a according to either FIG. 2 or FIG. 8 may vary depending on the size of biopsy needle, the tissue sample size, and the size of pledget to be delivered. One example of the adaptor 12a of FIG. 8 for delivery of an absorbable sponge pledget 18 through an approximately 18 gauge biopsy needle has a first adaptor diameter $D_1$ of about 0.25 cm or greater, preferably about 0.30 to 0.80 cm and a second adaptor diameter $D_2$ of about 0.25 cm or less, preferably, about 0.05 to 0.23 cm. An angle made by a wall of the tapered section 42a with a longitudinal axis of the adaptor 12a may vary from about 5° to 90°, but is preferably between about 30° and 60°. The tapered section 42a is illustrated with a substantially planar interior surface, when shown in cross section. However, the tapered section 42a may also have a convex or concave surface in cross section. The dimensions described for the adaptor 12a are appropriate for use with an approximately 18 gauge biopsy needle commonly used for liver biopsies. For some of the much larger biopsy needles or cannulas used for skin or breast biopsies the adaptor dimensions would be scaled up accordingly.

FIG. 8 also shows a connector 70 for connecting the adaptor 12 to a syringe 14 when the proximal end of the adaptor is larger in diameter than the standard syringe fitting. The connector 70 includes a first end 72 for connection to the syringe 14 and a second end 74 for connection to the adaptor 12.

One type of absorbable sponge material which is acceptable for use in the present invention is Gelfoam, manufactured by the Upjohn Company. Gelfoam is a porous, pliable, cross-linked gelatin material and is available commercially in sheet form as pre-compressed or non-compressed sponge. The material may be provided preformed as a pledget 18 or may be cut with a punch 10 or a stencil and knife to form a pledget as described above. Once hydrated, the pledget 18 can be easily compressed to fit into a lumen having a smaller cross sectional area than the original cross sectional area of the pledget. Additionally, the kneading of the hydrated pledget 18 during delivery encourages air trapped within the Gelfoam to be expelled and replaced with fluid, allowing rapid expansion upon delivery. When a pledget 18 of a pre-compressed Gelfoam is hydrated and kneaded (expelling air) during delivery, the pledget will have the absorbtion capacity to rapidly expand to many times (e.g., 3 or more times) its original dry volume upon delivery. When a pledget 18 of the non-compressed Gelfoam is hydrated and kneaded (expelling air) during delivery, the pledget will have the absorbtion capacity to rapidly expand to its original dry volume upon delivery. These properties make the Gelfoam sponge material particularly useful for facilitating hemostasis of biopsy sites.

Abrupt lumen diameter changes within or between the adaptor 12 or the needle 16 will improve "kneading" of the absorbable sponge material improving hydration of the absorbable sponge material thereby improving the expansion properties of the hydrated delivered absorbable sponge. According to the alternative embodiments of the adaptor illustrated in FIGS. 9 and 10, enlarged, recessed, or irregular areas in the lumen of the adaptor are provided to impart additional kneading action to the absorbable sponge material further improving expansion properties of the sponge.

The adaptor 12b of FIG. 9 includes two enlarged areas 72 of the lumen. As the absorbable sponge pledget 18 passes through the lumen of the adaptor 12b the material expands and is compressed by the adaptor to increase kneading of the pledget. FIG. 10 illustrates another alternative embodiment of the adaptor 12c including a lumen with a plurality of staggered irregularities 74 for improved kneading of the absorbable sponge pledget 18. The irregularities 74 will preferably have a relatively smooth surface to prevent the absorbable sponge material from becoming caught on the irregularities.

Although the pledget 18 has been shown and described as having a rectangular cross section, pledgets of other shapes may also be used. For example, the pledget may be preformed in any shape, such as with a rectangular or circular cross section or may be rolled from a thin sheet of absorbable sponge material. The pledget 18 may have a multi-sided cross section, a star shaped cross section, or a folded cross section and may have through or blind holes formed in the dry pledget. In addition, the pledget size and shape can be matched to the size and shape of a particular delivery site. Pledget shapes having greater surface area provided by features such as fins provide faster hydration.

The continuous structure of the absorbable sponge pledget 18 provides more secure and reliable placement than a paste or liquid and can even facilitate partial withdrawal, removal, or movement of the delivered pledget.

In some instances it may be desirable to deliver multiple pledgets in spaced apart positions along the biopsy tract, particularly for a long biopsy tract. For delivery of additional pledgets, the biopsy needle 16 is retracted a distance sufficient to provide a space to accommodate an additional pledget 18 and the injection procedure described above is repeated for the additional pledget(s). For a particularly large biopsy site or cavity, additional pledgets 18 may be injected beside an initially injected pledget until the cavity is filled.

Although biopsy is most commonly performed by biopsy needle, biopsy may also be performed through other cannulas, such as catheters, long needles, endoscopes, or the like. The treatment procedure according to the present invention can be used for facilitating hemostasis of puncture wounds through different types of cannulas including needles, catheters, endoscopes, and the like.

The absorbable sponge pledget 18 may be used to deliver a beneficial agent, such as contrast agent, thrombin, radiation treatment, or the like. The pledget can also be used to deliver therapeutic agents, such as radioactive isotopes for localized treatment of tumors, anti-cancer agents, anti-metastatic agents, and the like. Examples of anti-cancer agents include 5-fluorouracil, cisplatin, prednisone, and others described in U.S. Pat. No. 4,619,913 which is incorporated herein by reference. The absorbable sponge pledget 18 may be presoaked with the beneficial agent for delivery to the biopsy tract. Alternatively, the pledget 18 may be hydrated with the beneficial liquid agent or the agent may be delivered to the pledget after the pledget is placed within the biopsy tract.

A pledget formed of commercially available Gelfoam material will be absorbed by the body within 1 to 6 weeks. However, the pledget material may be designed to provide different rates of absorption. For example, Gelfoam can be designed to be absorbed at different rates by varying the degree of cross-linking. Preferably, the pledget is designed to be absorbed in less than one month.

The treatment of a biopsy tract with a hydrated and injected pledget 18 of absorbable sponge to facilitate hemostasis provides substantial advantages in comfort over external pressure methods. In addition, the present invention also provides advantages over the insertion of an absorbable sponge material in a dry state with an applicator. In particular, the adaptor 12 allows a relatively large pledget to be compressed and inserted into the biopsy tract in a hydrated state. The injected pledget 18 conforms in shape quickly to the shape of the biopsy tract and immediately begins blocking blood flow. In contrast, a dry piece of sponge material must be cut to the particular size of the biopsy tract and does not swell to fill the tract until the blood has sufficiently saturated the sponge material which can take up to several hours and provides inadequate local compression.

While the invention has been described in detail with reference to the preferred embodiments thereof, it will be apparent to one skilled in the art that various changes and modifications can be made and equivalents employed, without departing from the present invention.

What is claimed is:

1. A system for facilitating hemostasis of a puncture wound by injecting an absorbable sponge, the system comprising:
   a cannula for delivering the absorbable sponge in a hydrated state to the puncture wound;
   an adaptor connectable to the cannula for hydrating and delivering the absorbable sponge to the cannula, the adaptor having a tapered lumen with a large diameter end and a small diameter end, wherein the small diameter end is connectable to the cannula; and
   a syringe for injecting fluid into the adaptor to hydrate the absorbable sponge within the adaptor, and to deliver the absorbable sponge through the cannula.

2. The system for facilitating hemostasis of a puncture wound according to claim 1, wherein the adaptor lumen has at least one enlargement for kneading the absorbable sponge.

3. The system for facilitating hemostasis of a puncture wound according to claim 1, wherein the adaptor lumen has at least one irregularity for kneading the absorbable sponge.

4. The system for facilitating hemostasis of a puncture wound according to claim 1, wherein the adaptor has a lumen diameter at the small diameter end which is substantially equal to or less than a lumen diameter of the cannula.

5. The system for facilitating hemostasis of a puncture wound according to claim 1, wherein the syringe is connected to the adaptor by a luer fitting.

6. The system for facilitating hemostasis of a puncture wound according to claim 1, wherein the large diameter end of the lumen has a lumen diameter which is two or more times a lumen diameter at the small diameter end.

7. The system for facilitating hemostasis of a puncture wound according to claim 1, further comprising a cutting template for cutting a pledget of the absorbable sponge from a sheet of absorbable sponge material in a size suitable for delivery through the adaptor and the cannula.

8. The system for facilitating hemostasis of a puncture wound according to claim 1, further comprising a punching device for cutting a pledget of the absorbable sponge from a sheet of the absorbable sponge material in a size suitable for delivery through the adaptor and the cannula.

9. The system for facilitating hemostasis of a puncture wound according to claim 1, wherein the adaptor includes at least one vent hole in a wall of the adaptor adjacent the small diameter end of the lumen.

10. The system for facilitating hemostasis of a puncture wound according to claim 1, wherein the adaptor is transparent.

11. The system for facilitating hemostasis of a puncture wound according to claim 3, wherein the at least one irregularity is an enlargement of the lumen.

12. An adaptor for delivering a hydrated absorbable sponge to a cannula for facilitating hemostasis of a puncture wound, the adaptor comprising:
   an elongated member having a first end, a second end, and a lumen extending from the first end to the second end;
   a luer connector provided at the second end for connection to a cannula; and
   a tapered section of the lumen tapering from a first diameter at the first end to a second diameter at the second end which is smaller than the first diameter such that a dry sponge pledget having a width larger than the second diameter is compressible when hydrated into the second diameter.

13. The adaptor according to claim 12, wherein the tapered section makes an angle with a longitudinal axis of the adaptor of about 30° to 60°.

14. The adaptor according to claim 12, wherein the first diameter is at least about two times the second diameter.

15. The adaptor according to claim 12, wherein the adaptor lumen includes at least one irregularity for kneading a hydrated absorbable sponge.

16. The adaptor according to claim 15, wherein the at least one irregularity is an enlargement of the lumen.

17. The adaptor according to claim 12, in combination with an absorbable sponge material preloaded into the adaptor.

18. A method of facilitating hemostasis of a puncture wound by injecting an absorbable sponge through a cannula into the puncture wound, the method comprising:
   inserting a pledget of the absorbable sponge into an adaptor having a tapered lumen with a large diameter end and a small diameter end;
   hydrating the pledget by injection of fluid into the adaptor;
   connecting the adaptor to a cannula; and
   delivering the hydrated absorbable sponge through the cannula to facilitate hemostasis of the puncture wound.

19. The method according to claim 18, wherein the absorbable sponge is Gelfoam.

20. The method according to claim 18, wherein the puncture wound is a biopsy tract and the cannula through which the absorbable sponge pledget is delivered is a biopsy needle.

21. The method according to claim 18, wherein the pledget of the absorbable sponge is visually monitored within the adaptor.

22. A method of facilitating hemostasis of a biopsy tract comprising:
   removing a tissue biopsy through a cannula; and
   injecting a hydrated absorbable sponge pledget through the cannula without fully removing the cannula from the biopsy tract to facilitate hemostasis of the biopsy tract.

23. The method according to claim 22, wherein the cannula is partially withdrawn prior to injection of the hydrated absorbable sponge pledget to provide a space for the pledget in the biopsy tract.

24. The method according to claim 23, further comprising the steps of partially withdrawing the cannula after injection of the absorbable sponge to provide a space between a distal tip of the cannula and the injected absorbable sponge and injecting a second hydrated absorbable sponge through the cannula.

25. The method according to claim 22, wherein the step of injecting a hydrated absorbable sponge pledget through the cannula is achieved by a forced delivery of a fluid.

26. A kit for facilitating hemostasis of a puncture wound comprising:
   a pledget forming device;
   an adaptor connectable to a cannula for hydrating and delivering an absorbable sponge pledget to the cannula, the adapter having a tapered lumen with a large diameter end and a small diameter end, wherein the small diameter end is connectable to the cannula; and a syringe connectable to the adaptor for delivering fluid to the adaptor.

27. An adaptor preloaded with an absorbable sponge pledget comprising:

an elongated member having a first end, a second end, and a lumen extending from the first end to the second end, wherein the first end of the adaptor has a larger internal diameter than the second end of the adaptor; and an elongated pledget of absorbable sponge material loaded within the elongated member.

28. The adaptor according to claim 27, further comprising a tapered section between the first end and the second end which compresses the pledget when fluid is injected into the second end.

29. A system for facilitating hemostasis of a puncture wound by injecting an absorbable sponge, the system comprising:

a cannula for delivering the absorbable sponge in a hydrated state to the puncture wound;

an adaptor connectable to the cannula for hydrating and delivering the absorbable sponge to the cannula, the adaptor having a tapered lumen with a large diameter end and a small diameter end, wherein the small diameter end is connectable to the cannula;

a syringe for injecting fluid into the adaptor to hydrate the absorbable sponge within the adaptor, and to deliver the absorbable sponge through the cannula; and a cutting template for cutting a pledget of the absorbable sponge from a sheet of absorbable sponge material in a size suitable for delivery through the adaptor and the cannula.

30. A system for facilitating hemostasis of a puncture wound by injecting an absorbable sponge, the system comprising:

a cannula for delivering the absorbable sponge in a hydrated state to the puncture wound;

an adaptor connectable to the cannula for hydrating and delivering the absorbable sponge to the cannula, the adaptor having a tapered lumen with a large diameter end and a small diameter end, wherein the small diameter end is connectable to the cannula;

a syringe for injecting fluid into the adaptor to hydrate the absorbable sponge within the adaptor, and to deliver the absorbable sponge through the cannula; and a punching device for cutting a pledget of the absorbable sponge from a sheet of the absorbable sponge material in a size suitable for delivery through the adaptor and the cannula.

\* \* \* \* \*